United States Patent [19]

Wuest et al.

[11] Patent Number: 4,916,645

[45] Date of Patent: Apr. 10, 1990

[54] CONTINUOUS MONOCHROMETER DRIFT COMPENSATION OF A SPECTRAL MONOCHROMATOR

[75] Inventors: Charles E. Wuest, Norwalk; John B. Collins, Westport, both of Conn.

[73] Assignee: The Perkin-Elmer Corporation, Norwalk, Conn.

[21] Appl. No.: 201,250

[22] Filed: Jun. 2, 1988

[51] Int. Cl.⁴ .................. G06F 15/20; G01C 25/00
[52] U.S. Cl. .................... 364/571.04; 364/561.01; 73/1 R; 356/331; 356/332
[58] Field of Search .............. 364/571.04, 571.01, 364/571.02, 525, 559, 167.01; 73/1 R; 356/319, 308, 326, 331, 332, 334

[56] References Cited

U.S. PATENT DOCUMENTS

| | | | |
|---|---|---|---|
| 3,922,091 | 11/1975 | Suva et al. | 356/319 |
| 3,973,849 | 8/1976 | Jackson et al. | 356/308 |
| 4,223,995 | 9/1980 | Fletcher | 356/320 |
| 4,471,447 | 9/1984 | William et al. | 364/525 |
| 4,508,451 | 4/1985 | Stockdale | 356/325 |
| 4,519,706 | 5/1985 | Morley et al. | 356/332 |

Primary Examiner—P. S. Lall
Assistant Examiner—V. Trans
Attorney, Agent, or Firm—E. T. Grimes; H. S. Ingham

[57] ABSTRACT

Iterative compensation of drift of peak positions of spectral lines is effected in a spectral monochromator including a grating, a detector of spectral fractions of a spectral band, a stepper motor for varying relative orientation of the grating and the detector, and a computer. Computer-defined spectral windows each encopasses a spectral band and has an initial spectral center. Each window is scanned to determine a peak spectral position. Calculation is made for determining a spectral position error of the peak position from the initial center for each corresponding window. A functional average of the offsets for the peaks is calculated as a linear function of window position, and a revised spectral center for each window is calculated as being equal to the initial center plus the functional average for the window position determined from the linear function. Each window is shifted correspondingly. The step of successively scanning through each window is repeated to determine a new peak position for each corresponding band, whereby each new peak position is maintained near the spectral center of each corresponding window.

15 Claims, 7 Drawing Sheets

CONTINUOUS MONOCHROMETER DRIFT COMPENSATION OF A SPECTRAL MONOCHROMATOR

This invention relates to spectral monochromators and particularly to a method and a computerized system for compensating for drift of peak positions of spectral lines in a monochromator.

BACKGROUND OF THE INVENTION

Various types of optical spectrometers are in use for such purposes as atomic emission spectroscopy, atomic absorption spectroscopy and astronomy. A complete system generally consists of a source of radiation, a spectrometer for separating and detecting individual spectral components, and a data station for processing the information from the spectrometer. The radiation source, for example, may be a system for injecting a test sample into an inductively coupled plasma where the atomic species in the sample are excited to radiate characteristic atomic emission. As another example, a sample is evaporated in a graphite furnace where the gaseous sample absorbs certain frequencies of the incident radiation to provide atomic absorption lines. Similarly, astronomical sources provide atomic emission and absorption lines.

The type of spectrometer of particular interest herein involves sequential measurement utilizing a monochromator in which a grating or prism is rotated to direct a narrow portion of the spectrum to a slit and a detector. The angle is adjusted to correspond to the different emission (or absorption) lines of the elements. A single detector is used, either a solid state detector or a photomultiplier tube. The measurement process involves rotation of the grating with measurements at each of a series of selected locations corresponding to grating angles appropriate to the atomic emission lines.

Sophisticated monochromators, particularly of the type used for quantitative analysis of atomic elements in samples injected through an induction coupled plasma, are controlled by microprocessors and personal computers. Such a system is typified by a Model Plasma 40 emission spectrometer sold by The Perkin-Elmer Corporation, Norwalk, Conn., and described in co-pending U.S. patent application Ser. No. 837,438 filed Mar. 7, 1986, issued as U.S. Pat. No. 4,779,216 (Collins) assigned to the assignee of the present application. A stepper motor orients a grating with respect to the slit of the detector to locate any selected portion of the spectrum for measurement of the intensity of that portion. A dedicated microprocessor provides a suitable signal to the motor for selective orientation in relation to wavelength. The microprocessor also receives the intensity signal from the detector, and provides data in the form of spectral intensity vs spectral position. In practice a scanning signal is provided to the motor to sequentially scan the spectrum in a series of steps.

In order to allow a reasonably fast scan, signals to the motor are such as to scan in spectral windows which are just wide enough to encompass each of the selected spectral bands with some margin. The motor scans through all steps in a window, and then moves quickly to the next window before scanning in steps again, and on to the next window, etc., for the whole series of spectral bands.

The aforementioned Collins reference discloses a system for initially calibrating the window positions for the desired spectral lines in a monochromator to compensate for mechanical imperfections in its diffraction grating and grating drive assembly. The disclosed system employs a two-stage interactive procedure. Each stage involves measuring position errors of lines for a standard element and fitting these errors to a quadratic polynominal by the least squares method, as a function of window position. An iterative, self-consistent, discrete Fourier transform is used for the determination of multiple positioning correction terms. When the Fourier calculations are completed, the results of the calibration procedure are presented by the system to the analyst for acceptance. If accepted, the positioning error of the primary calibration line is measured, stored and used by the system to establish a zero centered distribution of positioning errors each time the monochromator is reinitialized.

However, the above-described calibration may be insufficient, especially for long-term operations. Temperature changes cause minute distortions in the spectrometer resulting in drifting of the positions of the spectral bands with respect to their windows. Without compensation, over a period of time a peak may drift through an edge of its window resulting in erroneous, undetected data. As temperature controlled rooms are often impractical or insufficient, a common method for minimizing drift is to temperature control the monochromator with a built-in heater and optionally a thermostat. Such a temperature control system has been found to be less than satisfactory because it is difficult to control all components uniformly without adding substantial cost and complexity to the apparatus.

SUMMARY OF THE INVENTION

Therefore an object of the present invention is to provide continuously updated compensation in a spectral monochromator for instrument drift, such as may be due to temperature variations. A further object is to provide such compensation at relatively modest cost. Another object is to provide such compensation by means of computer data processing.

The foregoing and other objects are achieved in a spectral monochromator including radiation means for generating elemental radiation for atomic elements, optical dispersion means receptive of the elemental radiation for producing a series of spectral bands each having a peak spectral position associated with maximum radiation intensity, and detector means selectively receptive of each spectral fraction of each spectral band for producing an intensity signal representative of the intensity of the spectral fraction being received. Scanning means are responsive of a scanning signal for varying relative orientation of the dispersion means and the detector means such that the series of spectral bands is scanned across the detector means in spectral positions corresponding to successive spectral fractions. A computer is receptive of the intensity signal for generating the scanning signal and calculating spectral position of each peak.

According to an embodiment of the present invention a method comprises, sequentially, establishing a set of spectral windows each encompassing one of a series of selected spectral bands and having a nominal spectral position and an initial spectral window center, successively scanning through each window such as to determine a peak spectral position for each corresponding band, calculating a spectral position error of the peak position from the initial center for each corresponding window, calculating a drift offset equal to a functional average of the position errors, calculating a revised spectral center for each window equal to the initial center plus the corresponding drift offset for the nominal window position, and shifting each window so as to center on its corresponding revised center The step of successively scanning through each window is repeated such as to determine a new peak position for each corresponding band. Thus each new peak position is maintained near the spectral center of each corresponding window. The method is especially suitable when successively repeating the sequence of steps on successive samples.

Preferably the step of calculating, the functional average comprises calculating a linear function of offsets vs. nominal window position, and determining the average offset for each nominal window position from the linear function.

DETAILED DESCRIPTION OF THE INVENTION

Figures 1, 2:
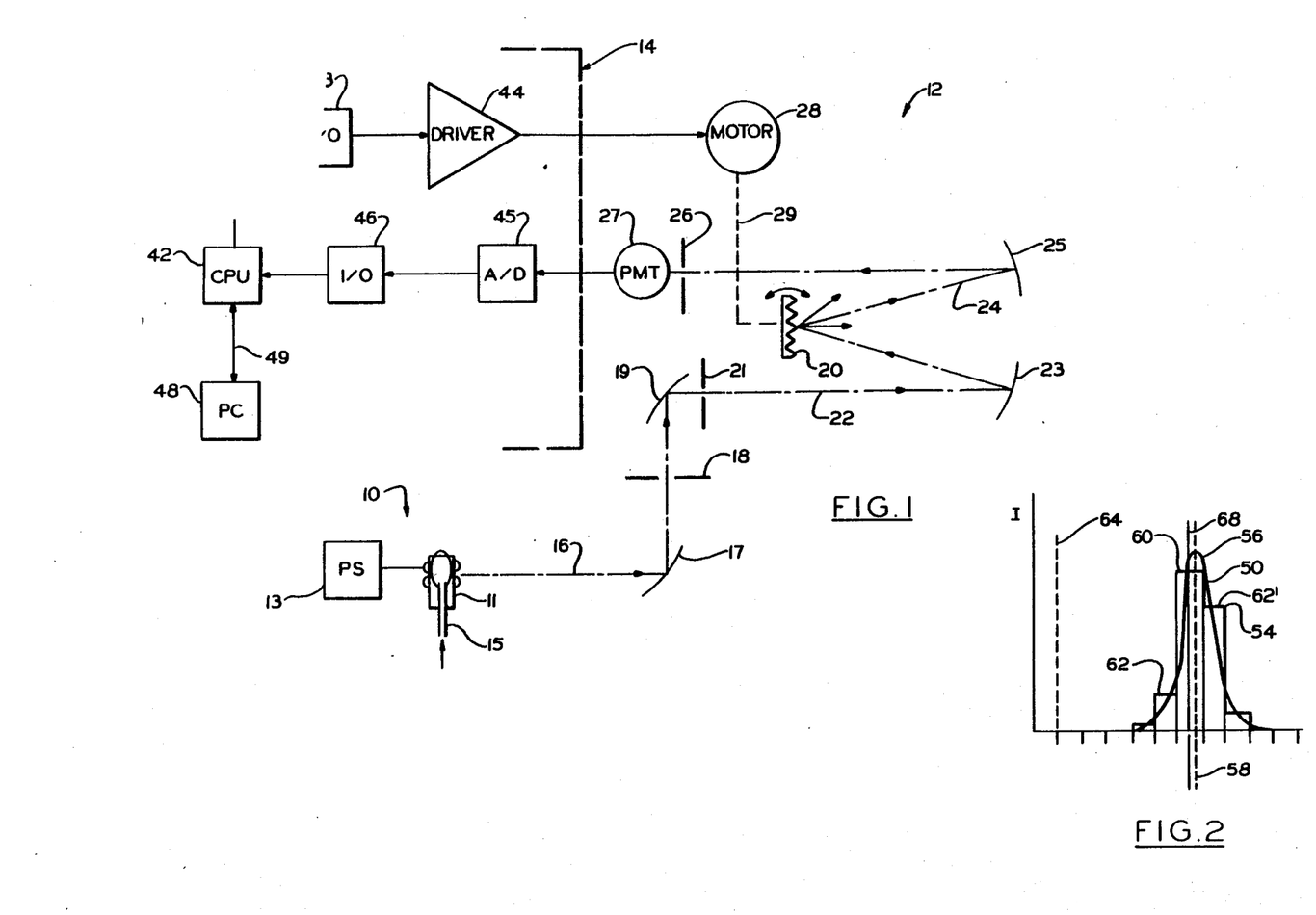
FIG. 1 is a schematic drawing of a spectral monochromator for carrying out the invention.
FIG. 2 is a graphical plot of a spectral band processed according to the invention.

A spectral monochromator system for carrying out the present invention is shown schematically in FIG. 1, which, for purposes of illustration herein, is of a type comparable to the aforementioned Perkin-Elmer Plasma 40 emission spectrometer. There are, broadly, three components, namely, a source of radiation 10, an optical spectrometer 12, and a data station 14.

Radiation source 10 produces infrared, visible and/or ultraviolet radiation generally characteristic of atomic elements. The source may be, for example, an inductively coupled plasma 11, driven by a power supply 13, into which a sample of test material (sometimes known as analyte) is injected by a sample aspirator 15. Alternatively the source may be a graphite furnace or the like operating to provide emission lines or absorption lines of atomic elements, or extraterrestrial with light being collected by an astronomical telescope.

Sample aspirator 15 injects into the plasma a mixture of a sample (e.g. unknown) material for ionization and analysis, and (optional) selected reference atomic elements as desired for calibration and/or standardization. Thus an input beam 16 from the source is characteristic of a plurality of atomic elements including the sample and references (if any).

The subsequent components, namely optical system 12 and data station 14, provide a quantitative measurement of the atomic elements associated with source 10. Optical system 12 is of the conventional or desired type that produces a display of spectral lines, and in the present example is of the grating type.

Light 16 from source 10 reflects from a first toroid mirror 17, passes through an entrance pupil 18, reflects from a second toroid mirror 19, and passes through an entrance slit 21. Rays 22 are then reflected by a concave collimator 23 to a reflective grating 20. Dispersed rays 24 reflected in a spectral pattern from the grating are passed to a concave spherical reflector 25 which focuses the rays selectively through an exit slit 26 to a detector 27. The detector is preferably a photomultiplier tube (PMT) for maximum sensitivity, although a solid state detector may be used.

A stepper motor 28 is operatively connected to rotate the grating by way of a conventional drive mechanism 29 of gears, pulleys and belts or the like such as disclosed in the aforementioned Collins reference. The stepper motor thus orients grating 20 with respect to slit 26 of the detector means to locate any selected portion of the spectrum for measurement of the intensity of that portion.

A dedicated microprocessor unit 42 (CPU) provides a suitable signal through an input/output board 43 and a driver 44 to motor 28 for selective orientation. Microprocessor 42 also receives an intensity signal from detector 27 after an analog/digital converter 45 and a second input/output board 46, and provides output data in the form of spectral intensity for each spectral position. The latter position is fundamentally wavelength (or frequency) but for purposes of internal computations and control is conveniently the step position of the motor. As in standard practice a scanning signal is provided to the motor such as to sequentially scan portions of the spectrum.

To provide for further control and also to implement the present invention as described hereinbelow, a second data processing unit 48 such as a personal computer (PC) is programmed for further processing of the information on intensity and position. The PC communicates with microprocessor 42 via an IEEE-488 cable 49. PC 48, CPU 42, and the interconnecting components with spectrometer 12, collectively constitute data station 14. Data station 14 alternatively may be incorporated into a single computer part of a central system to effect the required data processing, and is broadly termed "computer" or "computer means" herein and in the claims.

The spectral "lines" from the atomic elements of a sample being analyzed are each actually in the form of a bell shaped band 50, as illustrated in FIG. 2. This band is shown drawn on a horizontal position axis P with the step positions 52 of the stepper motor with widths marked thereon corresponding to the spectral width of slit 26 (FIG. 1). The detector measures intensity displayed on the vertical axis I of each spectral fraction corresponding to a step position, as indicated by the stepped intensity line 54 in FIG. 2. The purpose of the monochromator being to provide quantitative data on line intensities and, correspondingly, atomic elements, the intensity of the peak 56 associated with maximum radiation intensity is also determined. The peak intensity and spectral position 58 of the peak are computed conventionally in the computer by three point fitting of a parabola to the step 60 with highest intensity and the two steps 62,62' on either side of the maximum. The actual position of peak 56 thus may be expressed within a fraction of a step position, for the purposes of further calculation presented hereinbelow.

In order to provide for a fast scan, signals from computer 14 to motor 28 (FIG. 1) are such as to scan only in spectral "windows" which are selected to encompass with some margin each of the bands that are selected for measurement. A typical window is shown in FIG. 2 as defined between the two edges 64,66 shown as broken vertical lines. Thus microprocessor 42 is programmed to provide scanning signals for the motor to scan through all steps 52 in a window, and then move rapidly to the next selected window where the scanning steps are made again, and on to the next window, etc., for the whole series of spectral bands in a run. With each step being e.g. 0.022 nm for an ultraviolet grating, a window should be between about 8 and 70 steps wide, for example 30 steps. The computer program establishing the windows and signaling the motor accordingly is, for example, the same as used in the aforementioned Collins reference.

Because of the precision nature of the optical spectrometer, temperature changes cause minute distortions in the apparatus resulting in drifting of the positions of the spectral bands. In other words, a stepper motor setting that aligns a peak within a window in one run may not exactly do so in the next run; in other words, the peaks drift with respect to their windows. Without compensation, over a period of time a peak 56 may drift through an edge 64 or 66, and out of the window, resulting in unmeasured intensities and erroneous data, and this is the problem to which the present invention is directed. More specifically the invention is directed to maintaining each peak near a spectral center 68 (FIG. 2) of the corresponding window.

As an additional conventional step, for the purpose of determining intensities a radiation run is preliminarily made across each window without any elements being introduced. This background is subtracted from certain measured intensities to provide a net intensity indicated hereinafter. It will be appreciated that, for less accuracy or very low background, this step may not be necessary.

Figure 3:
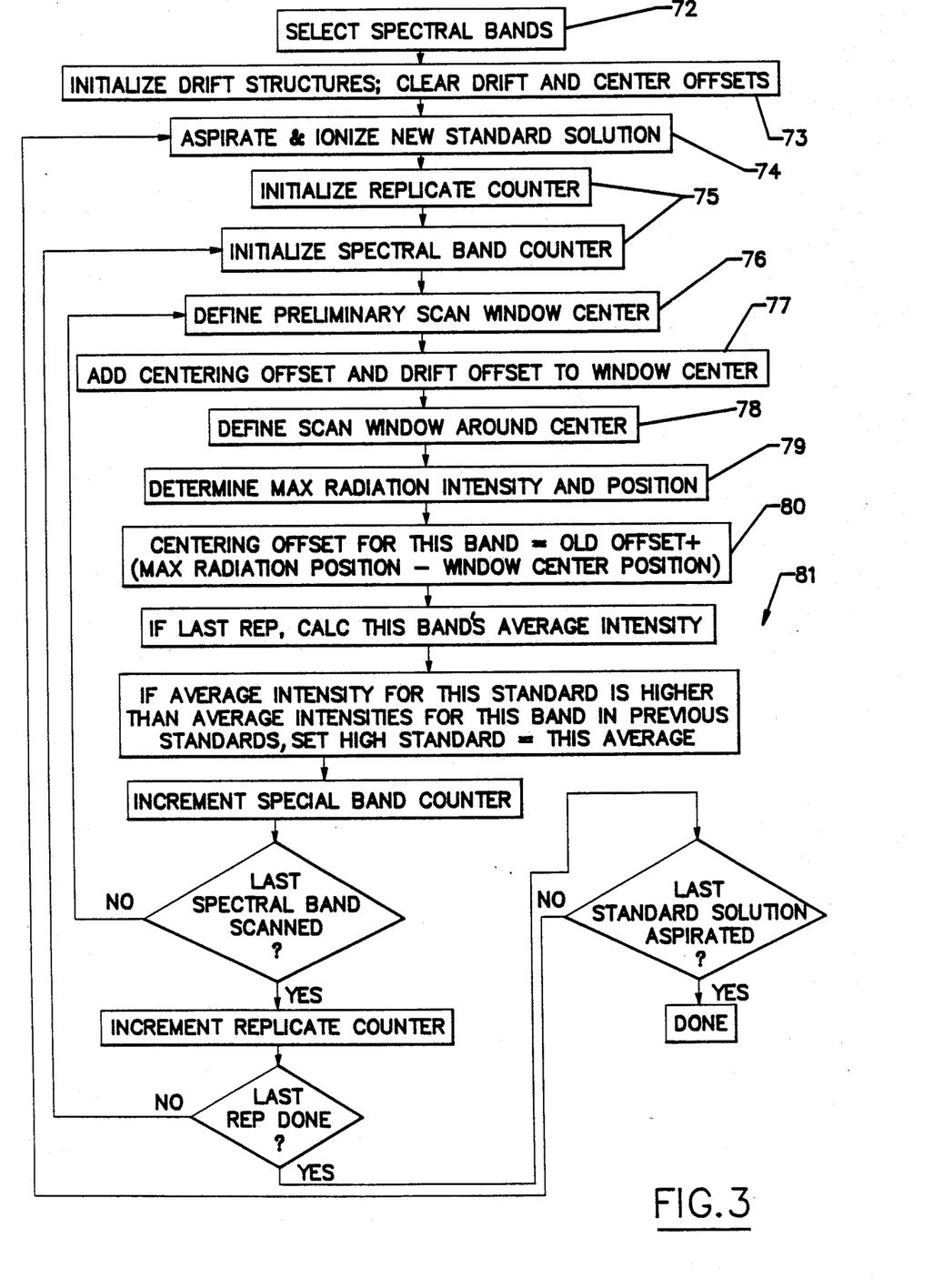
FIG. 3 is a flow diagram of a program in a component of the monochromator of FIG. 1 for establishing an initial spectral position of a window according to the invention.

A flow diagram illustrating the initial (standardization) steps is presented in FIG. 3 for a run in which the initial positions of corresponding windows are selected and defined by running standards. This sequence is generally conventional as in the Perkin-Elmer Plasma 40, but is presented herein for clarity.

Referring to FIG. 3, the desired spectral bands for analysis are selected (72), and drift structures and offsets are initialized (73). A standard sample is aspirated into the plasma (74) for ionization, and counters are initialized (75). Estimated preliminary peak positions for the selected spectral bands of at least one standard source containing known atomic elements with spectral lines for each of the selected bands are utilized for defining preliminary spectral window centers (76),i.e., centers of the windows. This run may be made with wider than normal windows defined to assure finding the peaks initially, for example twice as wide.

Offset corrections are made to the window center at this point (77). Initially these are zero. Centering offset is determined as part of the standardization of FIG. 3; drift offset may apply at this point in a restandardization only if determined subsequently according to the present invention and then a restandardization run is made. The window position is redefined to its new center (78), and the spectral band is scanned for its maximum radiation intensity and position (79). A new offset is computed (80) as the old offset (after previous run if any; zero if no prior run) plus the difference (e.g. in motor steps) between the peak location and the current window center. The subsequent steps (81) are directed to calculating intensity, determination of a highest intensity for several runs ("replicates") on standards, counting, moving to the next window, and running with further standards. After the last standard run, at (82) the standardized "center offset" for each window (at 80) is added to the preliminary center location (as corrected at 77) to define an initial spectral window center utilized as a basis for the further steps described below.

Figure 4:
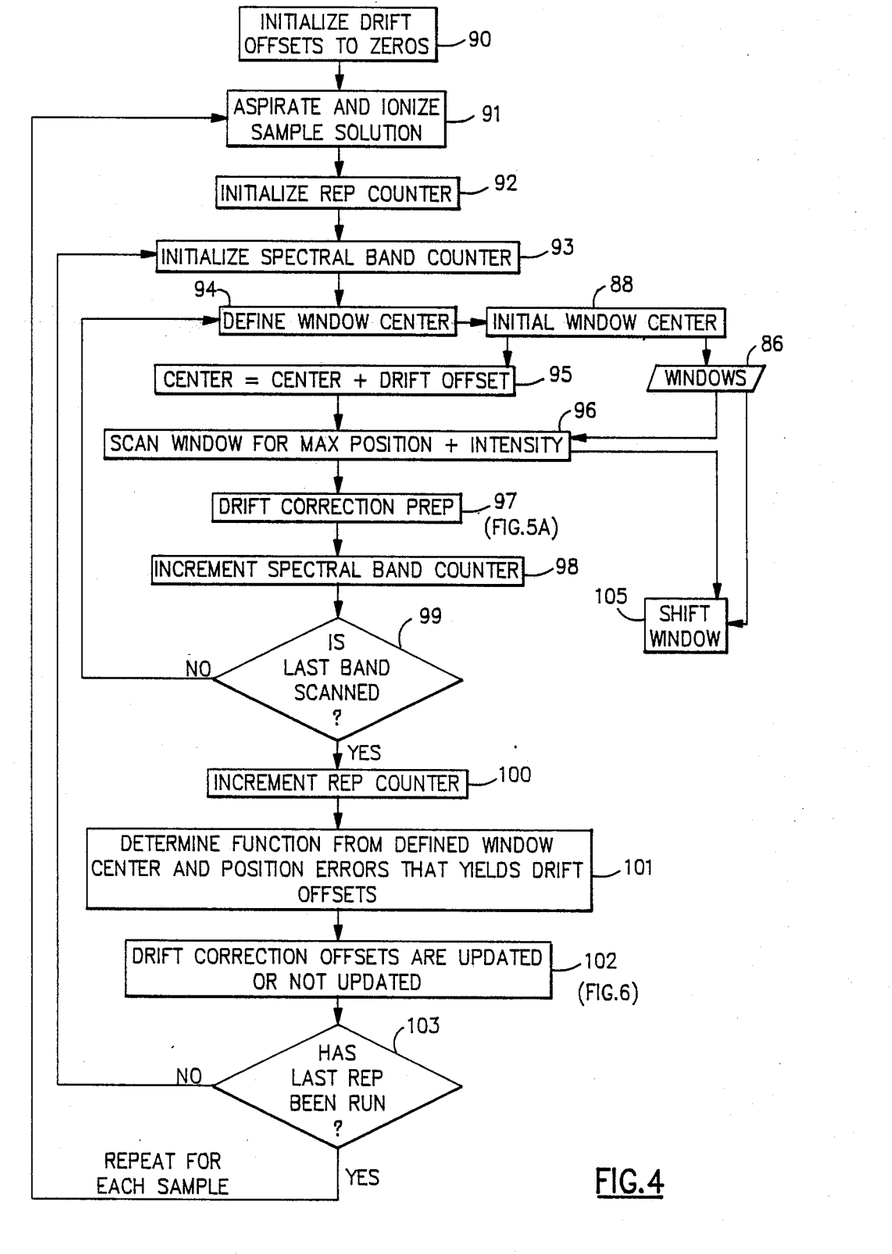
FIG. 4 is a flow diagram of a program in a component of the monochromator of FIG. 1 for compensating for drift according to the invention.

The method steps and means in a compensating system generally in the computer means of FIG. 1 for carrying out sample runs which make drift offset corrections according to the invention are depicted in the flow diagram of FIG. 4 and its associated figures. Elements of this and subsequent diagrams also represent schematically portions of the system, including the computer program, that carry out the invention, i.e. the means for carrying out the steps.

After initializing offsets to zero (90) (the first time) radiation is provided from a sample analyze (91), typically an unknown for which a quantitative atomic analysis is being determined. Counters are initialized (92,93). The center of the window is preliminarily defined (94), and an initial window center (88) is further defined as the preliminary center plus the center offset (determined with respect to FIG. 3 above). The window center is then corrected (95) for a drift offset which is as described below and is zero the first run. The window is scanned at a first scanning means (96) connected to the windows (86), and the spectral position and intensity of a peak, if any, is measured and stored. The peak drift error (offset) is prepared and screened by error means (97), as described further below, and some peaks may be rejected; i.e. not used in a correction calculation. A counter is incremented (98) and the next window band is scanned (99,94). For a next replicate another counter is incremented (100).

A drift offset equal to a functional average of position errors is determined next at offset means (101). Generally there is some scatter among the values for the various drift offsets, and a functional average value was deemed to be necessary. A simple average may be quite satisfactory. However, it was further determined that use of a simple average (sum of offsets divided by the number of peaks) may not provide suitable correction across the entire spectrum, frequently being too high or too low at the ends of the spectrum.

It was then discovered that there tends to be a general increase in offset with window position when the temperature is rising, and a similar decrease in offset with window position when the temperature is dropping, at least with the Plasma 40 instrument being used. (Other instruments could have opposite trends, but the principles and application of the invention herein still should apply.) Therefore, according to a preferred method step of the present invention, and continuing with reference to FIG. 4, a functional average offset is determined from a simple function of offsets vs. nominal window position (101). It generally is satisfactory that the simple function be a linear function. For better accuracy it may be desirable as a refinement to add a small quadratic term to the linear function to account for some apparent curvature. However, any complex function accurately describing the scattered values would defeat the purpose of providing an average offset value for each window. The phrase "functional average" as used herein and in the claims means either a simple average or an average determined from a simple function.

The simple function, e.g. an equation for a line, is readily determined by the computer using conventional algorithms for the least squares method. There should be at least two offsets available from a run to determine the function. The average offset for a window is determined by entering its nominal position into the equation. A further test (described below) is made to determine whether to even use the function to update offsets (102).

It is convenient and sufficiently accurate to utilize nominal position for the window for calculating the function to determine average offsets, such as the preliminary center or a boundary of the window. The number of total step scanning positions across a spectrum may approach 300,000 or more, so small differences in defining nominal window position for the linear function are inconsequential.

Upon selection of the same or another sample (103), the program with the drift offset returns to step 91 or 93, and the next window is selected (94). A revised spectral center for each window is calculated (95) as equal to its initial center position plus the corresponding updated drift offset from step 101 of the prior run. The window is shifted by shifting means 105 so as to have its center aligned with its revised center. Another run is made, with the same or other sample, and the sequences of FIG. 4 for determining offsets and adjusting window positions are repeated for successively continuing runs on other samples. It may be seen that any drift due to temperature changes or the like are compensated with continuous updates. The invention is particularly useful for many repeated runs made automatically over an extended period of time, and each peak position is generally maintained near the spectral center of each window.

Figure 5A:
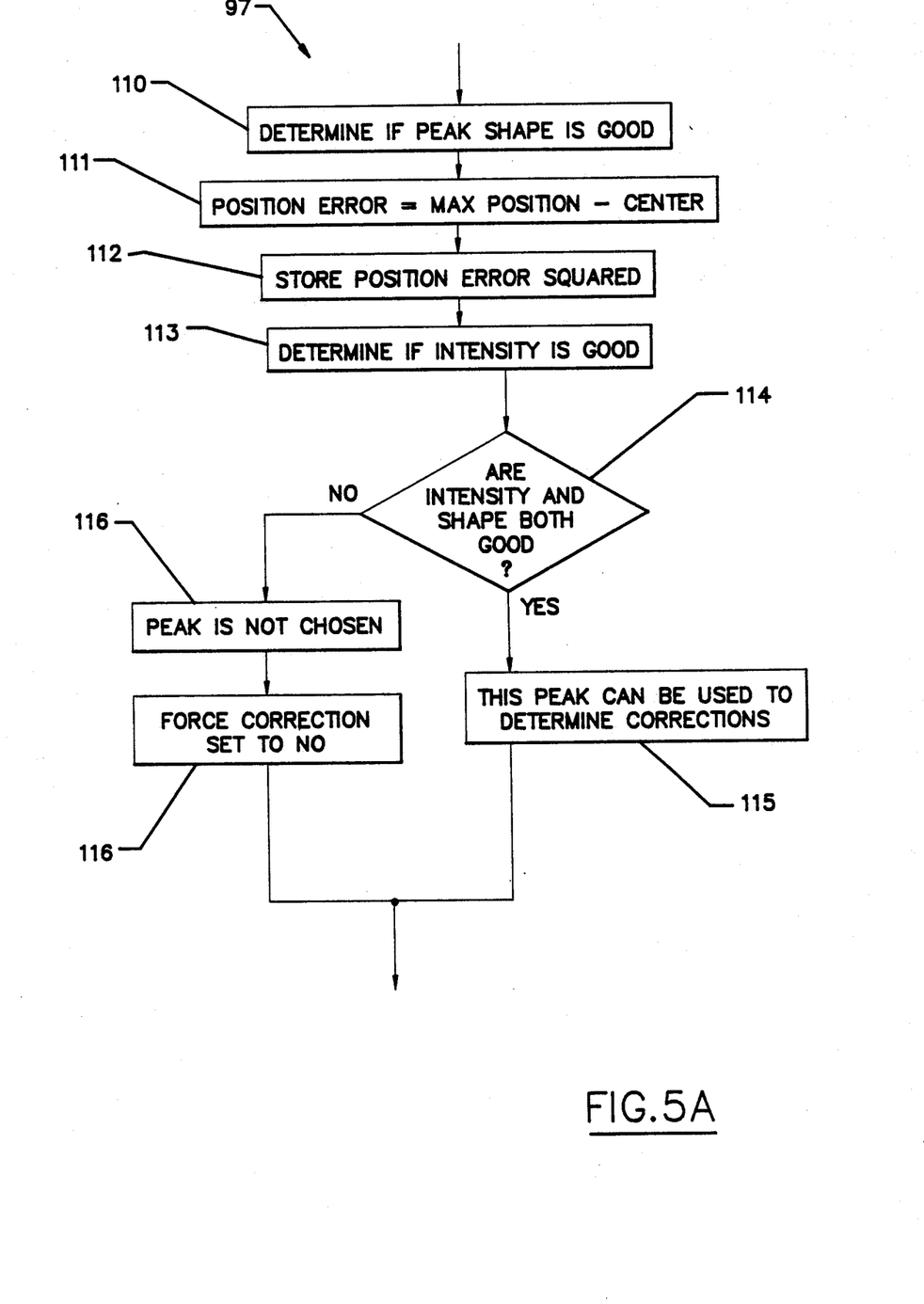
FIGS. 5A, 5B and 6 are flow diagrams for groups of steps indicated in FIG. 4.
Figure 5B:
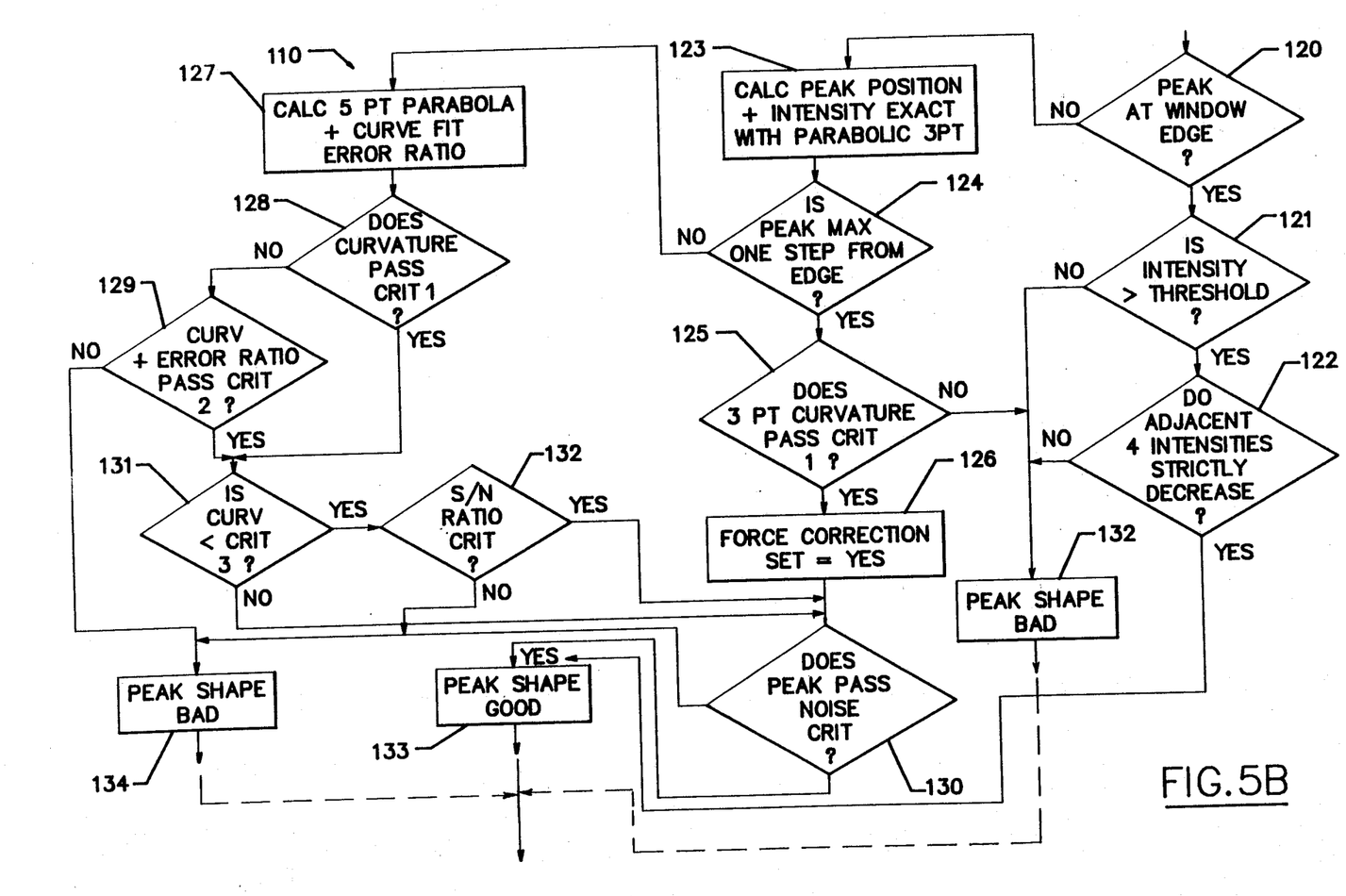

Drift offset preparation (97) including screening of the peaks is effected in order to account for situations where the data available for determining offsets may have no or questionable validity. This screening for peak shape and intensity is made readily in the computer by subroutines with conventional conditional statements which determine if values are greater or less than predetermined thresholds. Referring to FIGS. 5A, 5B and 5C each of a set of subroutines helps determine whether each offset is sufficiently valid for use in calculating the function. Peaks are selected or rejected for purposes of offset calculations, not necessarily for the analytical analysis based on intensities. The subroutines are carried out for each window.

FIG. 5A summarizes the program flow for drift correction (offset) preparation(97). Determination is made for good shape (110) (detailed below for FIG. 5B), and position error (offset) is computed. Position error is also squared and the result is stored (112) for future use. Determination is made next for good intensity (113) (as detailed below for FIG. 5C). If shape and intensity are both good (114), the position error is stored and the program with position error is passed back to point 97 in FIG. 4; if not, the program returns to point 97 with the offset value marked as unusable (116), for proceeding to the next steps. A "force correction" is utilized later in the program.

FIG. 5B illustrates the conditional statements for determining good peak shape, taken from point 110 (FIG. 5A).

One situation is interference from one or more other peaks in the window. If a peak is not at a window edge (120), a three point fit to a parabola (123), by a conventional algorithm comprising determining for each window a parabolic line computed from the parabolic equation $Y = AX_2 + BX + C$ where A, B and C are parabolic parameters, X represents successive spectral positions of spectral fractions in the corresponding window, Y represents the intensity of each corresponding spectral fraction. The computation of the parabolic line is made by fitting intensities for three points consisting of the peak and two spectral fractions adjacent to and on either side of the peak (60, 62, 62' of FIG. 2). A curvature parameter is defined as the value of parameter A, which should be a negative number. (A negative value for curvature indicates the upwardly pointing status of a peak.) Exact peak location and intensity are determined from the parabola (123) in the conventional manner.

If the peak is only one step away from an edge (124), the computer program asks whether the curvature is sufficient, vis. less than a first (negative) criterion value (125); a curvature criterion of $-95$ is suitable. If "yes", the program proceeds through a force correction set (126) (for future use) to a noise test (130). If "no", further refinement is desirable and a five point parabola is fitted (127) with the peak spectral fraction and each of the two spectral fractions on either side of the peak. Curvature parameter A is recalculated, and the sum of the squares of the errors of these five points from the parabola is calculated. This sum is divided by the curvature to define an error ratio (114).

Sets of preferable acceptance criteria for curvature and error ratio have been determined as set forth as examples in the Table herein; two such sets (128,129) are depicted in FIG. 5 for illustration. An offset is used for calculating the simple function only if the combined criteria in the set are met. As a minimum requirement, the curvature should be less than $-75$ and the error ratio should be greater than $-1000$.

TABLE

| Combined Criteria for Acceptance of Offset | |
|---|---|
| Curvature | Error Ratio |
| $< -43$ | (any) |
| $-43$ to $-30$ | $> -850$ |
| $-29.9$ to $-20$ | $> -420$ |
| $-20.9$ to $-11$ | $> -45$ |
| $-10.9$ to $-3$ | $> -2$ |

If the curvature and error ratio criteria are met, somewhere in the Table, and if the (negative) curvature is greater than a further threshold (131), e.g. greater than $-35$ (i.e. a relatively flat peak), then a signal/noise ratio is checked (132). Signal is peak intensity less background. Noise may be defined several ways. A suitable way is to use the intensity of the next highest peak in the window or, lacking same, the lowest intensity in the window; background is subtracted from either. The peak passes the test if the ratio is greater than a selected value such as 3.5.

The next test is another noise criterion (130), which may be any conventional or desired test. In the present example, the three point parabola (123) determines maximum intensity YMAX; the highest intensity of the three spectral fractions fitted is selected as Y2; the spectral intensity for the righthand spectral fraction adjacent to the highest intensity is Y3; and the value of curvature A is utilized. If YMAX $> 1.1$Y2 or if A/(Y2-Y3) $< -0.2$ the peak is deemed to be too noisy and is rejected from the offset error calculation.

A further problem to account for is a peak lying at or beyond the edge of a window. This may occur after a series of runs with samples having no elemental spectral band for the window and, therefore, no offset correction for a while. It is desirable to pull a line back into the window even at the expense of some accuracy for the linear function calculation. This pull-back is effected with a subroutine to recognize a tail of a peak off the edge, and, if so, apply two tests. The subroutine queries whether a peak intensity is measured abutting a window edge (120). If "yes", then the first test (121) is that the intensity of the spectral fraction at the edge be greater than a predetermined threshold such as 0.5% and preferably greater than 2% of a high intensity standard (described below). The second test (122) is that there should be at least two and preferably four additional spectral fractions adjacent the abutting fraction having successively decreasing intensities. A "no" for either test rejects the peak. Thus peak shape in subroutine group 110 is determined to be good (133) so the peak off can be used, or bad (134) so the peak cannot be used, and the flow is passed back to the main program.

The next screening situation is peak intensity. Referring to FIG. 5C, taken from point 113 (FIG. 5A), if a standard intensity exists (135), a net standard intensity IA is determined as a high intensity of a selected standard in high concentration, less background (136); and a net sample peak intensity IB is determined as the peak intensity, less background (137). A relative threshold intensity value IB/IA should be exceeded (138) before an offset may be utilized for calculating the average of offsets; otherwise the peak is rejected. An absolute minimum may be selected, but the system is more versatile if correlated with a set of standard peaks. For example, under routine calibration, several standards with different intensities are run for all selected spectral bands and windows. It is considered to be desirable to determine the threshold intensity as equal to a predetermined threshold percentage of a selected standard sample peak intensity, the selected peak being the highest of all the standards run for the window. A threshold of, for example 0.09% was found to be suitable. Thus intensity is either good (139) or bad (139') (peak rejected), and the program is returned to point 113 (FIG. 5A). If there is no standard intensity available for the peak (135), the ratio is set to zero (135') and the intensity will be treated as bad and rejected (139').

Figure 6:
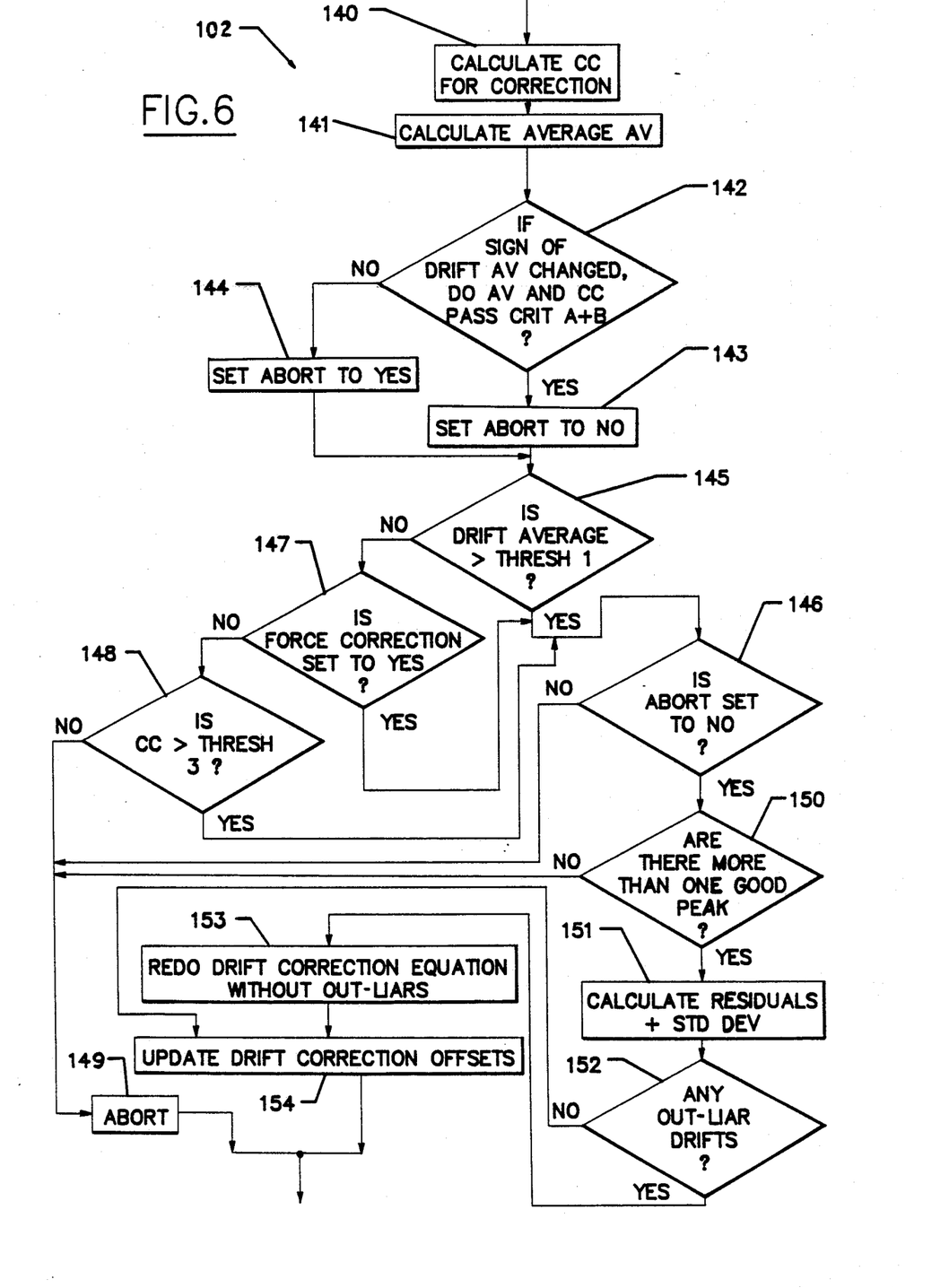

Further screening is shown in the flow sheet of FIG. 6, which is depicted at point 102 in FIG. 4, for testing data including the linear function itself for suitability. An unsuitable function is aborted with no offset correction being made for the next run.

Correlation coefficient, conventionally defined from a computation for the fit to the simple function, e.g. the least squares linear fit, is calculated (140). Normally the correlation coefficient should be greater than a first minimum selected value such as 0.25, for example greater than 0.31. This criterion is applied so long as the offset correction is successively increasing or successively decreasing such as due to consistently increasing or decreasing temperature. Yet another desirable criterion is the simple average of offsets for a run (total of offset values divided by their number (141), as distinguished from the average determined from the simple function of window position).

Data indicating a temperature reversal could be suspect, detected by a reversal in the sign of the simple average of offsets from the previous run (142). A related correction of window position is likely to be small anyhow. Thus if the simple average did change sign, a minimum correlation coefficient or other similar merit value of the function may be selected at a higher level such as twice the normal level, e.g. 0.62. If the higher correlation coefficient is not exceeded, no offset correction is made to the windows for the next run. Typical correlation coefficients were found to be generally around 0.9.

Returning to the flow diagram of FIG. 6, a determination is made whether the sign of simple average AV has changed (142); if so, the correlation coefficient (CC) is tested for being above the higher level criterion (e.g. 0.62). The simple average is also tested to determine that the absolute value of the simple average is greater than the absolute value for the previous run. If the sign has changed and if AV and CC exceed the criteria, an abort switch is set at "no" (143); otherwise at "yes" (144).

The simple average AV is again tested for its threshold criterion (145) (e.g.0.6) and, if "yes", the program proceeds to a query on abort set (146). If AV is less than the threshold, the program queries (147) if the force correction is set to "yes" (126 of FIG. 5B); if "yes" the program proceeds to the abort set query (146). This retains a peak if it is one step from an edge.

If force correction (147) is not set to "yes", the correlation coefficient is tested (148) to exceed its normal lower threshold (e.g.0.31). If "yes" the program similarly proceeds to the abort set query (146). If "no" the run data for drift is aborted (149), i.e., not utilized for a drift correction, and the program returns to point 102 (FIG. 4). The run is similarly aborted (149) and returned if the abort set (146) is not set on "no". If abort is set on "no" (146), it is determined whether there is more than one peak (150) available for the function; if not, the run is aborted (149).

If there are sufficient peaks (150), standard deviations are determined (151). If an offset is more than a selected multiple of its standard deviation, such as two and preferably three standard deviations away from the corresponding average offset (determined from the linear function) (152), it is considered an outlier and the offset is rejected. The sample function is recalculated without outliers (153) and the average of offsets is updated (154).

Figure 7:
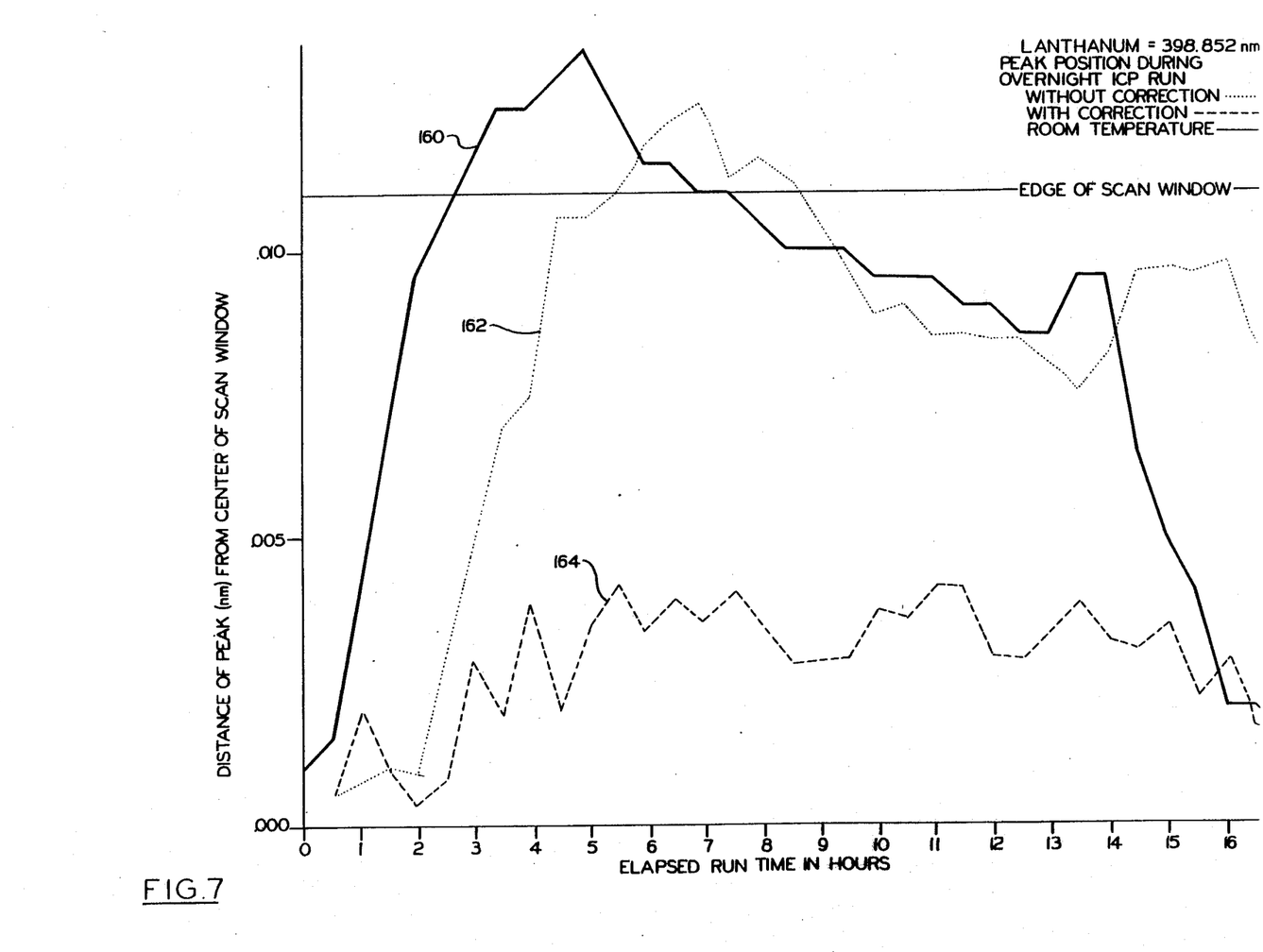
FIG. 7 is a graphical plot of results of a run made according to the invention.

As indicated above, the invention is particularly useful for many repeated runs made automatically over an extended period of time, with each peak position being maintained near the spectral center of each window. FIG. 7 illustrates the success of the present invention in compensating for temperature changes and drift, in particular the results of compensations made during a typical unattended eighteen hour overnight, using the Lanthanum 398.852 nm line. The solid line 160 indicates room temperature. The dotted line 162 indicates uncorrected positions of the selected peak. The dashed lines 164 indicate the corrected peak positions.

If the correction had not been used, the intensities recorded for Lanthanum 398.852 nm would have been inaccurate for 17% of the instrument run (that is, during all times at which the peak position exceeded the edge of the scan window). Instead, accurate intensities were recorded for 100% of the eighteen hour overnight instrument run.

While the invention has been described above in detail with reference to specific embodiments, various changes and modifications which fall within the spirit of the invention and scope of the appended claims will become apparent to those skilled in this art. The invention is therefore only intended to be limited by the appended claims or their equivalents.

What is claimed is:

1. A method of continuously compensating for drift of peak positions of spectral lines in a spectral monochromator including radiation means for generating elemental radiation for atomic elements, optical dispersion means receptive of the elemental radiation for producing a series of spectral bands each having a peak spectral position associated with maximum radiation intensity, dectector means selectively receptive of a spectral fraction of a spectral band for producing an intensity signal representative of the intensity of the spectral fraction being received, scanning means responsive of a scanning signal for varying relative orientation of the dispersion means and the detector means such that the series of spectral bands is scanned across the detector means in spectral positions corresponding to successive spectral fractions, and computer means receptive of the intensity signal for generating the scanning signal and calculating spectral position of each peak; the method comprising the steps of, in sequence:

establishing a series of spectral windows each encompassing a selected spectral band and having an initial window center, successively scanning through each of the windows so as to determine a maximum peak spectral position for a corresponding band, calculating a spectral position error of the peak position from the initial center for each corresponding window, calculating a drift offset equal to a functional average of the position errors, calculating a revised spectral center for each window equal to the initial center plus the corresponding drift offset, shifting each window to its revised center, and repeating the step of successively scanning through each of the windows so as to determine a new peak position for each corresponding band, whereby each new peak position is maintained near a spectral center of each corresponding window.

2. A method according to claim 1 wherein the dispersion means includes a dispersion member and the scanning means includes a stepper motor receptive of the scanning signal and operatively connected to the dispersion member.

3. A method according to claim 1 further comprising successively repeating in sequence the steps of calculating a spectral position error of the peak position from the initial center for each window, calculating a drift offset, calculating a revised spectral center, shifting each window, and repeating the step of successively scanning through each of the windows, such as to determine a further new peak position for each corresponding band, whereby each further new peak position is maintained near the spectral center of each corresponding window for successive spectral scans.

4. A method according to claim 1 further comprising the step of utilizing each position error for calculating the drift offset only if such offset meets a predetermined criterion.

5. A method according to claim 4 wherein the step of utilizing each position error comprises measuring a peak intensity for each peak and utilizing each position error for calculating the drift offset only if such peak intensity associated with such position error exceeds a predetermined threshold intensity.

6. A method according to claim 5 wherein the threshold intensity for each peak is determined as equal to a predetermined threshold percentage of a standard sample peak intensity.

7. A method according to claim 4 wherein the step of utilizing each position error comprises calculating a curvature parameter for each peak, and utilizing the corresponding position error for calculating the simple function only if the corresponding curvature parameter meets a predetermined curvature criterion.

8. A method according to claim 7 further comprising determining for each window a parabolic line computed from the parabolic equation $Y = AX_2 + BX + C$ where A, B and C are parabolic parameters, X represents successive spectral positions of spectral fractions in the corresponding window, Y represents the intensity of each corresponding spectral fraction, and the computation of the parabolic line is made by fitting intensities for at least three intensity points consisting of the peak and adjacent spectral fractions adjacent to and on either side of the peak, and wherein the curvature parameter is defined as parameter A and is less than a predetermined curvature value.

9. A method according to claim 8 wherein each of the intensity points has an intensity error from the parabola, and the method further comprises calculating an error ratio defined as the sum of the squares of the intensity errors divided by the curvature, and utilizing the corresponding offset for calculating the simple function only if the corresponding error ratio exceeds a predetermined error ratio.

10. A method according to claim 4 wherein the step of utilizing each position error comprises detecting each peak that is in a spectral fraction abutting an edge of a window, measuring a peak intensity for each such abutting spectral fraction, measuring corresponding intensities of at least two spectral fractions adjacent the abutting spectral fraction, and utilizing a corresponding position error for calculating the simple function only if the abutting intensity exceeds a predetermined threshold intensity and if the adjacent spectral fractions have successively decreasing intensities away from the peak abutting fraction.

11. A method according to claim 1 wherein the functional average is a simple function of nominal window position.

12. A method according to claim 11 wherein the step of calculating a drift offset comprises computing a linear function of offsets vs. nominal window position, and the functional average for each nominal window is determined from the linear function.

13. A method according to claim 11 further comprising calculating a standard deviation for the simple function, rejecting offsets that exceed a preselected multiple of the standard deviation, and recalculating the simple function without the rejected offsets prior to shifting each window.

14. A method according to claim 11 further comprising additional steps of calculating a merit value for the simple function and shifting each window only if the merit value meets a predetermined criterion.

15. A method according to claim 14 wherein the additional steps comprise calculating a correlation coefficient for the simple function, and shifting each window only if the correlation coefficient exceeds a predetermined correlation coefficient.

* * * * *